US009498450B2

(12) United States Patent
Ellers-Lenz et al.

(10) Patent No.: US 9,498,450 B2
(45) Date of Patent: Nov. 22, 2016

(54) 1-AMINOCYCLOHEXANE DERIVATIVES FOR THE TREATMENT OF COCHLEAR TINNITUS

(75) Inventors: Barbara Ellers-Lenz, Morfelden-Walldorf (DE); Tanja Rosenberg, Hamburg (DE); Hagen Kruger, Frankfurt Am Main (DE); Michael Althaus, Schoeueck (DE)

(73) Assignee: MERZ PHARMA GmbH & CO. KGaA, Frankfurt am Main (DE)

( * ) Notice: Subject to any disclaimer, the term of this patent is extended or adjusted under 35 U.S.C. 154(b) by 1768 days.

(21) Appl. No.: 12/733,646

(22) PCT Filed: Sep. 10, 2008

(86) PCT No.: PCT/EP2008/007421
§ 371 (c)(1),
(2), (4) Date: Nov. 15, 2010

(87) PCT Pub. No.: WO2009/033652
PCT Pub. Date: Mar. 19, 2009

(65) Prior Publication Data
US 2011/0077304 A1 Mar. 31, 2011

Related U.S. Application Data

(60) Provisional application No. 60/993,396, filed on Sep. 12, 2007, provisional application No. 61/066,931, filed on Feb. 25, 2008, provisional application No. 61/067,026, filed on Feb. 25, 2008, provisional application No. 61/067,083, filed on Feb. 25, 2008.

(30) Foreign Application Priority Data

| Sep. 12, 2007 | (EP) | 07253630 |
| Mar. 14, 2008 | (EP) | 08004776 |
| Mar. 14, 2008 | (EP) | 08004777 |
| Mar. 14, 2008 | (EP) | 08004778 |

(51) Int. Cl.
*A61K 31/13* (2006.01)
*A61K 9/20* (2006.01)

(52) U.S. Cl.
CPC ............. *A61K 31/13* (2013.01); *A61K 9/2054* (2013.01)

(58) Field of Classification Search
None
See application file for complete search history.

(56) References Cited

U.S. PATENT DOCUMENTS

| 6,034,134 | A | * | 3/2000 | Gold | 514/579 |
| 6,066,652 | A | * | 5/2000 | Zenner | 514/317 |
| 6,071,966 | A | | 6/2000 | Gold et al. | |
| 2003/0236286 | A1 | | 12/2003 | Deorazio et al. | |
| 2005/0011804 | A1 | * | 1/2005 | Zanden | 206/534 |
| 2005/0014743 | A1 | | 1/2005 | Gupta et al. | |
| 2006/0002999 | A1 | * | 1/2006 | Yang | 424/464 |
| 2006/0264897 | A1 | * | 11/2006 | Lobl | 604/506 |
| 2007/0141148 | A1 | | 6/2007 | Hauptmeier | |
| 2007/0299113 | A1 | * | 12/2007 | Kalvinsh | 514/338 |
| 2011/0092600 | A1 | * | 4/2011 | Plitt | 514/579 |

FOREIGN PATENT DOCUMENTS

| WO | WO 98/10757 | | 3/1998 |
| WO | WO 0215907 A1 | * | 2/2002 |
| WO | WO 2004022069 A1 | * | 3/2004 |
| WO | WO 2004/043899 | | 5/2004 |
| WO | WO 2005/009326 | | 2/2005 |
| WO | WO 2005/044228 | | 5/2005 |
| WO | WO2006/069294 | | 6/2006 |
| WO | WO 2006/079055 | | 7/2006 |
| WO | WO 2006079055 A2 | * | 7/2006 |
| WO | WO 2006/096194 | | 9/2006 |
| WO | WO 2006096194 A2 | * | 9/2006 |
| WO | WO2007062815 | | 6/2007 |
| WO | WO 2007062815 A1 | * | 6/2007 |

OTHER PUBLICATIONS

U.S. Appl. No. 12/998,033, filed Mar. 2011, Ellerz-Lenz et al.*
U.S. Appl. No. 12/737,092, filed Dec. 2010, Ellerz-Lenz et al.*
U.S. Appl. No. 12/733,582, filed Mar. 2010, Kruger.*
U.S. Appl. No. 12/733,577, filed Mar. 2010, Ellerz-Lenz et al.*
U.S. Appl. No. 13/068,984, filed May 2011, Althaus et al.*
U.S. Appl. No. 12/733,645, filed Mar. 2010, Ellerz-Lenz et al.*
Xiong et. al., Bioorg. & Med. Chem., 9, pp. 1773-1780, (2001).*
Posakony et. al., J. Med. Chem., 47, pp. 2635-2644, (2004).*
Eggermont, DDT, vol. 10(19): 1283, 1291, Oct. 2005.*
Haynes et al., Arthritis and Rheumatism, vol. 24, No. 3, p. 501-503, Mar. 1981.*
European Search Report for 08004776.4 of Jun. 2, 2008.
International Search Report and Written Opinion for PCT/EP2008/007421 of Jan. 28, 2009.
J. Eggermont, "Tinnitus: neurobiological substrates" DDT, Vo. 10, No. 19, p. 1283-1291, Oct. 2005.
P. Plazas, et al., Inhibition of the α9-α10 nicotinic cholinergic receptor by neramexane, and open channel blocker of N-methyl-D-aspartate receptor, European Journal of Pharmacology, vol. 566, p. 11-19, 2007.
European Search Report for European Application No. 07253630.3 of Dec. 6, 2007.
European Search Report for European Application No. 08004777.2 of Jul. 2, 2008.
European Search Report for European Application No. 08004778.0 of Aug. 5, 2008.

* cited by examiner

Primary Examiner — Svetlana M Ivanova
(74) Attorney, Agent, or Firm — Hueschen and Sage

(57) ABSTRACT

The present invention relates to the treatment of an individual afflicted with cochlear tinnitus comprising administering to the individual an effective amount of a 1-aminoalkylcyclohexane derivative.

20 Claims, 1 Drawing Sheet

Stratified analysis of TBF-12 total score change to baseline by presence of cochlear tinnitus, neramexane 50 mg/d group, intent-to-treat population, last observation carried forward
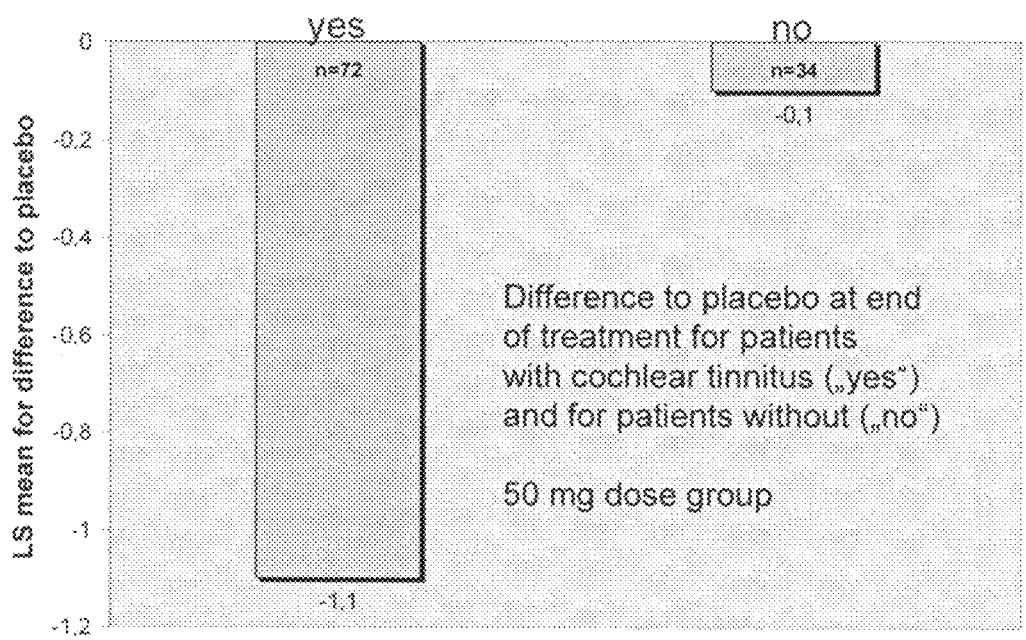

1-AMINOCYCLOHEXANE DERIVATIVES FOR THE TREATMENT OF COCHLEAR TINNITUS

FIELD OF THE INVENTION

The present invention relates to the treatment of an individual afflicted with cochlear tinnitus comprising administering to the individual an effective amount of a 1-aminoalkylcyclohexane derivative.

BACKGROUND OF THE INVENTION

Tinnitus is commonly referred to as 'ringing in the ears'—the perception of sounds in the absence of an external source of acoustic signals. Tinnitus has been defined as "the perception of a sound which results exclusively from the activity within the nervous system without any corresponding mechanical, vibratory activity within the cochlea, that is, tinnitus as an auditory phantom perception" (Jastreboff et al., J Am Acad Audiol 2000; 11(3): 162-177). Tinnitus is frequently associated with a decreased sound tolerance (i.e. hyperacusis).

The pathophysiology of subjective tinnitus is poorly understood and a definitive pathogenesis of tinnitus is unknown. Many environmental and substance-induced factors may cause tinnitus. Among the most frequently cited factors are acute acoustic trauma, occupational noise, and recreational music. In general, tinnitus seems to be the result of neuronal dysfunction within the auditory pathway. This dysfunction is misleadingly perceived as sound by higher auditory centers and can lead to functional alterations within the auditory nervous system. Maladaptive functional changes in cortical structures could result in an altered balance between excitatory and inhibitory neurotransmission and may lead to more severe tinnitus. In all cases, a potential malfunction in auditory pathways and auditory cortex is related to the activity of the prefrontal cortex and limbic system.

In most cases (95%), the perceived tinnitus is purely subjective in nature, e.g. no physical source of acoustic signals can be identified and, therefore, cannot be heard externally. A physical examination is performed to exclude objective tinnitus, e.g. the patient's perception of sound is caused by a real source of sound waves, e.g. the sound from turbulent flow in blood vessels reaching the cochlea. Tinnitus may be classified according to duration of tinnitus and the degree of tinnitus expression (e.g. severity or annoyance of the tinnitus) (McCombe et al., Clin Otolaryngol 2001; 26(5): 388-393 and Davis et al., Epidemiology of Tinnitus. In: Tyler R, editor. Tinnitus Handbook. San Diego: Singular Publishing Group; 2000. p. 1-23). Regarding the impact of tinnitus, tinnitus may be severely annoying to the patient and may be accompanied by social and psychological complications.

It has also been suggested that tinnitus may be further classified into two groups, peripheral tinnitus and central tinnitus, based on differences in how the tinnitus is perceived by the affected individual. Peripheral (or cochlear) tinnitus is presumed to originate from the peripheral nervous system and cochlea, and central tinnitus is presumed to originate in the auditory cortex.

Cochlear physiology provides some understanding of the origins of that form of the disease associated with the cochlea. Two rows of hair cells are found in the cochlea. Outer hair cells (OHC) actively contract in the presence of sound, and thus augment incoming low-oscillation signals and modulate the response of inner hair cells (IHC). Exposure to noise, including constant, repeated or even one single "blast trauma", can damage cochlear hair cells, especially their fragile stereocilia. Since the OHC require substantially more oxygen than the IHC, they are more sensitive to noise, ototoxic drugs, trauma, etc. Due to the loss of active amplification, damage to the OHC can result in reduction of the dynamic range of the auditory system and impaired frequency selectivity. Uncontrolled contraction of damaged OHC can lead to stimulation of IHC and to nerve action potentials that are interpreted as sounds by the brain. Damage to the IHC can lead to abnormal deflection of the stereocilia, causing the cells to depolarize, leading to uncontrolled release of neurotransmitters which, again, can cause the perception of sound without a real source (Baguley, Br Med Bull. 2002; 63:195-212).

With the passage of time, higher levels of the auditory pathway may be involved, and the perception of tinnitus may not depend on the cochlear pathology any longer. A massive central amplification takes place, triggered by pathological cognitive focussing. Presumably, amplifying feedback mechanisms between the limbic system and cognitive areas of the CNS are established (Zenner, Ziel. Dtsch Arztebl. 2001; 37:2361-2365).

While a large number of afferent, mainly glutamatergic nerve fibers originate at the IHC (Furness, et al., J Neurosci. 2003 Dec. 10; 23(36):11296-11304), the OHC are the target of efferent nerve fibers with acetylcholine being the principal efferent neurotransmitter in the cochlea (Dallos et al, J Neurosci. 1997 Mar. 15; 17(6):2212-2226). An excess of glutamate in cochlear neurons is believed to contribute to tinnitus. Therefore, several approaches to tinnitus treatment have been made by using NMDA receptor-blocking substances, such as acamprosate or caroverine. Studies with these substances have shown limited success, possibly because the treatment target was mainly the afferent part of the auditory system while efferent neurotransmission was only marginally influenced.

Maison et al (J Neurosci. 2002 Dec. 15; 22(24):10838-10846) also describe efferent protection from acoustic trauma by overexpression of the α9/α10 nicotinic acetylcholine receptor complex.

So far, however, there are no well-established, specific medical treatments for tinnitus that provide replicable reduction of tinnitus and annoyance due to tinnitus, in excess of placebo effects (Dobie, Laryngoscope 1999; 109(8): 1202-1211; Eggermont et al., Trends Neurosci 2004; 27(11): 676-682; and Patterson et al., Int Tinnitus J 2006; 12(2): 149-159). Thus, a need exists for pharmaceutical products which are effective in treating or preventing tinnitus.

1-Amino-alkylcyclohexanes such as neramexane (also known as 1-amino-1,3,3,5,5-pentamethylcyclohexane) have been found to be useful in the therapy of various diseases especially in certain neurological diseases, including Alzheimer's disease and neuropathic pain. 1-Amino-alkylcyclohexanes such as neramexane are disclosed in detail in U.S. Pat. Nos. 6,034,134 and 6,071,966, the subject matter of which patents is hereby incorporated by reference. It is believed that the therapeutic action of 1-amino-alkylcyclohexanes such as neramexane is related to the inhibition of the effects of excessive glutamate at the N-methyl-D-aspartate (NMDA) receptors of nerve cells, for which reason the compounds are also categorized as NMDA antagonists, or NMDA receptor antagonists. Neramexane has also been disclosed to exhibit activity as an α9/α10 nicotinic receptor antagonist (Plazas, et al., Eur J Pharmacol., 2007 Jul. 2; 566(1-3):11-19).

U.S. Pat. No. 6,034,134 discloses that 1-amino-alkylcyclohexanes may be useful in the treatment of tinnitus due to their activity as NMDA receptor antagonists.

The instant inventors have discovered that 1-amino-alkylcyclohexanes, such as neramexane, are effective in treating cochlear tinnitus.

SUMMARY OF THE INVENTION

The present invention relates to a 1-amino-alkylcyclohexane derivative for the treatment or the prevention of cochlear tinnitus in a subject in need thereof.

In a further aspect the present invention relates to the use of a 1-amino-alkylcyclohexane derivative for the manufacture of a medicament for the treatment or prevention of cochlear tinnitus in a subject in need thereof. The 1-amino-alkylcyclohexane derivative may be neramexane or a pharmaceutically acceptable salt thereof such as neramexane mesylate.

In a further aspect of the invention such treatment occurs within three (3) to twelve (12) months of onset of tinnitus (e.g., treatment is started within three (3) to twelve months (including three (3) to eight (8) months) after tinnitus first appears). The 1-amino-alkylcyclohexane derivative may be neramexane or a pharmaceutically acceptable salt thereof such as neramexane mesylate.

In a further aspect of the invention within such treatment the individual is afflicted with tinnitus associated with hearing loss or tinnitus associated with mild hearing loss.

In a further aspect the invention relates to a 1-amino-alkylcyclohexane derivative for the treatment or the prevention of tinnitus associated with hearing loss or mild hearing loss and the use of a 1-amino-alkylcyclohexane derivative for the manufacture of a medicament for the treatment or prevention of tinnitus associated with hearing loss or mild hearing loss in a subject in need thereof.

In a further aspect the invention relates to a 1-amino-alkylcyclohexane derivative for the treatment or the prevention of tinnitus, wherein treatment occurs within three to twelve months of onset of tinnitus (sub-acute tinnitus), or wherein treatment occurs within three to eight months of onset of tinnitus and to the use of 1-amino-alkylcyclohexane derivative for the manufacture of a medicament for the treatment or prevention of tinnitus, wherein treatment occurs within three to twelve months of onset of tinnitus, or wherein treatment occurs within three to eight months of onset of tinnitus.

A further aspect of the invention relates to a 1-amino-alkylcyclohexane derivative (e.g., neramexane or a pharmaceutically acceptable salt thereof such as neramexane mesylate) in the form of an immediate or a modified release formulation for the treatment of cochlear tinnitus.

A further aspect of the invention relates to the above defined derivative or use, wherein to the individual a 1-amino-alkylcyclohexane derivative (e.g., neramexane or a pharmaceutically acceptable salt thereof such as neramexane mesylate) and at least one additional pharmaceutical agent which has been shown to be effective in treating tinnitus is administered.

A further aspect of the invention relates to the above-defined derivative or use, wherein to the individual a 1-amino-alkylcyclohexane derivative (e.g., neramexane or a pharmaceutically acceptable salt thereof such as neramexane mesylate) and at least one additional pharmaceutical agent selected from antidepressants or anti-anxiety drugs (such as selective serotonin reuptake inhibitors (SSRIs), serotonin-norepinephrine reuptake inhibitors (SNRIs), noradrenergic and specific serotonergic antidepressants (NASSAs), norepinephrine (noradrenaline) reuptake inhibitors (NRIs), norepinephrine-dopamine reuptake inhibitors, or serotonin 1A agonists), dopamine antagonists, Alpha2Delta ligands, and NK1 antagonists is administered.

A further aspect of the invention relates to a 1-amino-alkylcyclohexane derivative (e.g., neramexane or a pharmaceutically acceptable salt thereof such as neramexane mesylate) in combination with other therapies for tinnitus and, optionally, at least one pharmaceutically acceptable carrier or excipient.

A further aspect of the invention relates to a 1-amino-alkylcyclohexane derivative (e.g., neramexane or a pharmaceutically acceptable salt thereof such as neramexane mesylate) in combination with an additional pharmaceutical agent selected from antidepressants or anti-anxiety drugs (such as selective serotonin reuptake inhibitors (SSRIs), serotonin-norepinephrine reuptake inhibitors (SNRIs), noradrenergic and specific serotonergic antidepressants (NASSAs), norepinephrine (noradrenaline) reuptake inhibitors (NRIs), norepinephrine-dopamine reuptake inhibitors, or serotonin 1A agonists), dopamine antagonists, Alpha2Delta ligands, and NK1 antagonists, and, optionally, at least one pharmaceutically acceptable carrier or excipient.

A further aspect of the invention relates to a 1-amino-alkylcyclohexane derivative (e.g., neramexane or a pharmaceutically acceptable salt thereof such as neramexane mesylate) in combination with an additional pharmaceutical agent selected from antidepressants or anti-anxiety drugs (such as selective serotonin reuptake inhibitors (SSRIs), serotonin-norepinephrine reuptake inhibitors (SNRIs), noradrenergic and specific serotonergic antidepressants (NASSAs), norepinephrine (noradrenaline) reuptake inhibitors (NRIs), norepinephrine-dopamine reuptake inhibitors, or serotonin 1A agonists), dopamine antagonists, Alpha2Delta ligands, and NK1 antagonists, and, optionally, at least one pharmaceutically acceptable carrier or excipient for the treatment or the prevention of tinnitus.

The present invention further relates to a method of treating or preventing cochlear tinnitus in a subject in need thereof, comprising administering an effective amount of a 1-amino-alkylcyclohexane derivative, or a pharmaceutically acceptable salt thereof (e.g., neramexane or a pharmaceutically acceptable salt thereof such as neramexane mesylate), in a pharmaceutically acceptable carrier.

A further aspect of the invention relates to such a method wherein treatment occurs within three to twelve months of onset of tinnitus.

A further aspect of the invention relates to such a method wherein treatment occurs within three to eight months of onset of tinnitus.

A further aspect of the invention relates to such a method wherein the tinnitus is associated with hearing loss, including mild hearing loss.

A further aspect of the invention relates to such a method, wherein the 1-amino-alkylcyclohexane derivative (e.g., neramexane or a pharmaceutically acceptable salt thereof such as neramexane mesylate) is administered in a range from about 5 mg to about 150 mg/day, or wherein the 1-amino-alkylcyclohexane derivative (e.g., neramexane or a pharmaceutically acceptable salt thereof such as neramexane mesylate) is administered in a range from about 5 mg to about 100 mg/day, or wherein the 1-amino-alkylcyclohexane derivative (e.g., neramexane or a pharmaceutically acceptable salt thereof such as neramexane mesylate) is administered at about 5 mg to about 75 mg/day, or wherein the 1-amino-alkylcyclohexane derivative (e.g., neramexane or a pharmaceutically acceptable salt thereof such as neramexane mesylate) is administered at about 50 mg/day, or wherein the 1-amino-alkylcyclohexane derivative (e.g., neramexane or a pharmaceutically acceptable salt thereof such as neramexane mesylate) is administered at about 75 mg/day.

A further aspect of the invention relates to such a method wherein the 1-amino-alkylcyclohexane derivative (e.g., neramexane or a pharmaceutically acceptable salt thereof such as neramexane mesylate) is administered once a day, twice a day (b.i.d.), or three times a day.

A further aspect of the invention relates to such a method wherein the 1-amino-alkylcyclohexane derivative (e.g., neramexane or a pharmaceutically acceptable salt thereof such as neramexane mesylate) is administered twice a day (b.i.d.).

A further aspect of the invention relates to such a method wherein the 1-amino-alkylcyclohexane derivative (e.g., neramexane or a pharmaceutically acceptable salt thereof such as neramexane mesylate) is administered in an immediate release formulation.

A further aspect of the invention relates to such a method wherein the 1-amino-alkylcyclohexane derivative (e.g., neramexane or a pharmaceutically acceptable salt thereof such as neramexane mesylate) is administered in a modified release formulation.

The present invention further relates to a method of treating or preventing cochlear tinnitus in a subject in need thereof, comprising administering an effective amount of a 1-amino-alkylcyclohexane derivative, or a pharmaceutically acceptable salt thereof (e.g., neramexane or a pharmaceutically acceptable salt thereof such as neramexane mesylate), and an additional pharmaceutical agent which has been shown to be effective in treating or preventing tinnitus.

A further aspect of the invention relates to a method of treating or preventing tinnitus such as cochlear tinnitus in a subject in need thereof, comprising administering an effective amount of a 1-amino-alkylcyclohexane derivative, or a pharmaceutically acceptable salt thereof (e.g., neramexane or a pharmaceutically acceptable salt thereof such as neramexane mesylate), and an additional pharmaceutical agent, wherein the additional pharmaceutical agent is selected from antidepressants or anti-anxiety drugs (such as selective serotonin reuptake inhibitors (SSRIs), serotonin-norepinephrine reuptake inhibitors (SNRIs), noradrenergic and specific serotonergic antidepressants (NASSAs), norepinephrine (noradrenaline) reuptake inhibitors (NRIs), norepinephrine-dopamine reuptake inhibitors, or serotonin 1A agonists), dopamine antagonists, Alpha2Delta ligands, and NK1 antagonists.

A further aspect of the invention relates to such a method wherein the 1-amino-alkylcyclohexane derivative (e.g., neramexane or a pharmaceutically acceptable salt thereof such as neramexane mesylate) and the additional pharmaceutical agent are administered conjointly.

A further aspect of the invention relates to such a method wherein the 1-amino-alkylcyclohexane derivative (e.g., neramexane or a pharmaceutically acceptable salt thereof such as neramexane mesylate) and the additional pharmaceutical agent are administered in a single formulation.

The present invention further relates to a method of treating tinnitus in a subject in need thereof, comprising administering an effective amount of a 1-amino-alkylcyclohexane derivative, or a pharmaceutically acceptable salt thereof (e.g., neramexane or a pharmaceutically acceptable salt thereof such as neramexane mesylate), in a pharmaceutically acceptable carrier, wherein treatment occurs within three to twelve months of onset of tinnitus.

A further aspect of the invention relates to such a method wherein treatment occurs within three to eight months of onset of tinnitus.

The present invention further relates to a method of treating or preventing tinnitus associated with hearing loss (including mild hearing loss) in a subject in need thereof, comprising administering an effective amount of a 1-amino-alkylcyclohexane derivative, or a pharmaceutically acceptable salt thereof (e.g., neramexane or a pharmaceutically acceptable salt thereof such as neramexane mesylate), in a pharmaceutically acceptable carrier.

The present invention further relates to a pharmaceutical composition for the treatment or the prevention of cochlear tinnitus comprising a therapeutically effective amount a 1-amino-alkylcyclohexane derivative, or a pharmaceutically acceptable salt thereof (e.g., neramexane or a pharmaceutically acceptable salt thereof such as neramexane mesylate), and at least one pharmaceutically acceptable carrier or excipient.

The present invention further relates to a pharmaceutical composition comprising a therapeutically effective amount of a 1-amino-alkylcyclohexane derivative, or a pharmaceutically acceptable salt thereof (e.g., neramexane or a pharmaceutically acceptable salt thereof such as neramexane mesylate), in combination with an additional pharmaceutical agent which has been shown to be effective for the treatment or the prevention of tinnitus and, optionally, at least one pharmaceutically acceptable carrier or excipient.

BRIEF DESCRIPTION OF THE DRAWINGS

FIG. 1 shows data from a tinnitus pilot study with neramexane showing the change in Tinnitus-Beeinträchtigungs-Fragebogen (THF-12) (i.e., the German version of the Tinnitus Handicap Inventory or THI) score at the end of treatment for the 50 mg dose group compared to placebo.

DETAILED DESCRIPTION OF THE INVENTION

As used herein, the term "tinnitus" includes, but is not limited to, all manifestations of subjective and objective tinnitus as well a acute, subacute and chronic forms. It also includes cochlear tinnitus as well as tinnitus associated with hearing loss or mild hearing loss.

As used herein, the term "cochlear tinnitus" refers to tinnitus in a frequency range of hearing loss. The term cochlear tinnitus includes motor tinnitus, cochlear motor tinnitus or hair cell tinnitus. Cochlear tinnitus may be caused by toxic drugs (e.g. loop diuretics such as frusemide, aminoglycosides such as gentamicin) or loud sound exposure (e.g. acoustic trauma, chronic occupational noise).

As used herein the term "sub-acute tinnitus" includes tinnitus of a duration of three (3) to twelve (12) months.

As used herein the term "hearing loss" (or "hearing impairment") is a full or partial loss of the ability to detect sounds or to distinguish among different sounds. Hearing loss is diagnosed clinically by an increased hearing threshold level in a pure tone audiogram. The hearing threshold level of left/right ear in decibel (dB) may be calculated as the average of the actual numbers at different frequencies on a pure tone audiogram, ie. as the average hearing level threshold levels at 0.25, 0.5, 1, 2 and 4 kHz. There are different degrees of hearing loss. Hearing loss is defined herein as "mild hearing loss" (or "mild hearing impairment") if the hearing threshold level is within 20-40 decibel (dB). Noise-induced tinnitus associated with hearing loss may be caused by acute or chronic conditions. Long-term exposure to excessive noise is the more common cause of noise-induced tinnitus associated with hearing loss; however, such tinnitus associated with hearing loss may also be caused by extremely loud sounds. Sensorineural tinnitus associated with hearing loss is due to insensitivity of the inner ear or to impairment of function in the auditory nervous system. Sensorineural tinnitus associated with hearing loss may be caused by abnormalities in the hair cells of the organ of the Corti in the cochlea.

Within the present application the term "subject" encompasses mammals including animals and humans.

The term 1-amino-alkylcyclohexane derivative is used herein to describe a compound which is a 1-amino-alkylcyclohexane or a compound derived from 1-amino-alkylcyclohexane, e.g. pharmaceutically acceptable salts of 1-amino-alkylcyclohexanes. The present 1-amino-alkylcyclohexane derivatives may also be described as "1-amino-cyclohexane derivatives."

The 1-amino-alkylcyclohexane derivatives of the present invention may be represented by the general formula (I):

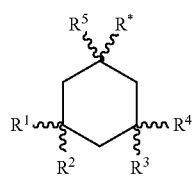

(I)

wherein R* is —(CH$_2$)$_n$—(CR$^6$R$^7$)$_m$—NR$^8$R$^9$
wherein n+m=0, 1, or 2
wherein R$^1$ through R$^7$ are independently selected from the group consisting of hydrogen and C$_{1-6}$alkyl, wherein R$^8$ and R$^9$ are independently selected from the group consisting of hydrogen and C$_{1-6}$alkyl or together represent lower-alkylene —(CH$_2$)$_x$— wherein x is 2 to 5, inclusive, and optical isomers, enantiomers, hydrates, and pharmaceutically-acceptable salts thereof.

Non-limiting examples of the 1-amino-alkylcyclohexanes used according to the present invention include:
1-amino-1,3,5-trimethylcyclohexane,
1-amino-1(trans),3(trans),5-trimethylcyclohexane,
1-amino-1(cis),3(cis),5-trimethylcyclohexane,
1-amino-1,3,3,5-tetramethylcyclohexane,
1-amino-1,3,3,5,5-pentamethylcyclohexane (neramexane),
1-amino-1,3,3,5-tetramethyl-3-ethylcyclohexane,
1-amino-1,5,5-trimethyl-3,3-diethylcyclohexane,
1-amino-1,5,5-trimethyl-cis-3-ethylcyclohexane,
1-amino-(1S,5S)cis-3-ethyl-1,5,5-trimethylcyclohexane,
1-amino-1,5,5-trimethyl-trans-3-ethylcyclohexane,
1-amino-(1R,5S)trans-3-ethyl-1,5,5-trimethylcyclohexane,
1-amino-1-ethyl-3,3,5,5-tetramethylcyclohexane,
1-amino-1-propyl-3,3,5,5-tetramethylcyclohexane,
N-methyl-1-amino-1,3,3,5,5-pentamethylcyclohexane,
N-ethyl-1-amino-1,3,3,5,5-pentamethyl-cyclohexane,
N-(1,3,3,5,5-pentamethylcyclohexyl)pyrrolidine,
3,3,5,5-tetramethylcyclohexylmethylamine,
1 amino-1,3,3,5(trans)-tetramethylcyclohexane (axial amino group),
3-propyl-1,3,5,5-tetramethylcyclohexylamine semihydrate,
1-amino-1,3,5,5-tetramethyl-3-ethylcyclohexane,
1-amino-1,3,5-trimethylcyclohexane,
1-amino-1,3-dimethyl-3-propylcyclohexane,
1-amino-1,3(trans),5(trans)-trimethyl-3(cis)-propylcyclohexane,
1-amino-1,3-dimethyl-3-ethylcyclohexane,
1-amino-1,3,3-trimethylcyclohexane,
cis-3-ethyl-(trans)-3(trans)-5-trimethylcyclohexamine,
1-amino-1,3(trans)-dimethylcyclohexane,
1,3,3-trimethyl-5,5-dipropylcyclohexylamine,
1-amino-1-methyl-3(trans)-propylcyclohexane,
1-methyl-3(cis)-propylcyclohexylamine,
1-amino-1-methyl-3(trans)-ethylcyclohexane,
1-amino-1,3,3-trimethyl-5(cis)-ethylcyclohexane,
1-amino-1,3,3-trimethyl-5(trans)-ethylcyclohexane,
cis-3-propyl-1,5,5-trimethylcyclohexylamine,
trans-3-propyl-1,5,5-trimethylcyclohexylamine,
N-ethyl-1,3,3,5,5-pentamethylcyclohexylamine,
N-methyl-1-amino-1,3,3,5,5-pentamethylcyclohexane,
1-amino-1-methylcyclohexane,
N,N-dimethyl-1-amino-1,3,3,5,5-pentamethylcyclohexane,
2-(3,3,5,5-tetramethylcyclohexyl)ethylamine,
2-methyl-1-(3,3,5,5-tetramethylcyclohexyl)propyl-2-amine,
2-(1,3,3,5,5-pentamethylcyclohexyl)-ethylamine semihydrate,
N-(1,3,3,5,5-pentamethylcyclohexyl)-pyrrolidine,
1-amino-1,3(trans),5(trans)-trimethylcyclohexane,
1-amino-1,3(cis), 5(cis)-trimethylcyclohexane,
1-amino-(1R,5S)trans-5-ethyl-1,3,3-trimethylcyclohexane,
1-amino-(1S,5S)cis-5-ethyl-1,3,3-trimethylcyclohexane,
1-amino-1,5,5-trimethyl-3(cis)-isopropyl-cyclohexane,
1-amino-1,5,5-trimethyl-3(trans)-isopropyl-cyclohexane,
1-amino-1-methyl-3(cis)-ethyl-cyclohexane,
1-amino-1-methyl-3(cis)-methyl-cyclohexane,
1-amino-5,5-diethyl-1,3,3-trimethyl-cyclohexane,
1-amino-1,3,3,5,5-pentamethylcyclohexane,
1-amino-1,5,5-trimethyl-3,3-diethylcyclohexane,
1-amino-1-ethyl-3,3,5,5-tetramethylcyclohexane,
N-ethyl-1-amino-1,3,3,5,5-pentamethylcyclohexane,
N-(1,3,5-trimethylcyclohexyl)pyrrolidine or piperidine,
N-[1,3(trans),5(trans)-trimethylcyclohexyl]pyrrolidine or piperidine,
N-[1,3(cis),5(cis)-trimethylcyclohexyl]pyrrolidine or piperidine,
N-(1,3,3,5-tetramethylcyclohexyl)pyrrolidine or piperidine,
N-(1,3,3,5,5-pentamethylcyclohexyl)pyrrolidine or piperidine,
N-(1,3,5,5-tetramethyl-3-ethylcyclohexyl)pyrrolidine or piperidine,
N-(1,5,5-trimethyl-3,3-diethylcyclohexyl)pyrrolidine or piperidine,
N-(1,3,3-trimethyl-cis-5-ethylcyclohexyl)pyrrolidine or piperidine,
N-[(1S,5S)cis-5-ethyl-1,3,3-trimethylcyclohexyl]pyrrolidine or piperidine,
N-(1,3,3-trimethyl-trans-5-ethylcyclohexyl)pyrrolidine or piperidine,
N-[(1R,5S)trans-5-ethyl,3,3-trimethylcyclohexyl]pyrrolidine or piperidine,
N-(1-ethyl-3,3,5,5-tetramethylycyclohexyl)pyrrolidine or piperidine,
N-(1-propyl-3,3,5,5-tetramethylcyclohexyl)pyrrolidine or piperidine,
N-(1,3,3,5,5-pentamethylcyclohexyl)pyrrolidine,
and optical isomers, diastereomers, enantiomers, hydrates, their pharmaceutically acceptable salts, and mixtures thereof.

1-Amino-alkylcyclohexane derivatives (e.g., neramexane, 1-amino-1,3,3,5,5-pentamethylcyclohexane) are disclosed in U.S. Pat. Nos. 6,034,134 and 6,071,966. 1-Aminoalkylcyclohexane derivatives (e.g., neramexane) may be used according to the invention in the form of any of pharmaceutically acceptable salts, solvates, isomers, conjugates, and prodrugs, any references to 1-amino-alkylcyclohexane derivatives (e.g., neramexane) in this description should be understood as also referring to such salts, solvates, isomers, conjugates, and prodrugs.

As used herein the term antidepressants or anti-anxiety drugs (such as selective serotonin reuptake inhibitors (SSRIs), serotonin-norepinephrine reuptake inhibitors (SNRIs), noradrenergic and specific serotonergic antidepressants (NASSAs), norepinephrine (noradrenaline) reuptake inhibitors (NRIs), norepinephrine-dopamine reuptake inhibitors, or serotonin 1A agonists) includes: fluoxetine, fluvoxamine paroxetine, citalopram, escitalopram, sertraline, bupropion, desipramine, reboxetine, viloxazine, amirtazapine, milnacipran, nefazodone, venlafaxine, desvenlafaxine, duloxetine, mirtazapine, atomoxetine, buspirone and pharmaceutically acceptable salts thereof.

As used herein the term dopamine antagonist includes trans-1-{4-[2-[4-(2,3-dichlorophenyl)-piperazin-1-yl]-ethyl]-cyclohexyl}-3,3-dimethyl-urea and pharmaceutically acceptable salts thereof.

As used herein the term Alpha2Delta ligand includes gabapentin, pregabalin, phenibut, PF-2393296, and PF-293765 and pharmaceutically acceptable salts thereof.

As used herein the term NK1 antagonist includes aprepitant, fosaprepitant, vestipitant, casopitant, AV-608, dilopetine, and LY-686017 and pharmaceutically acceptable salts thereof.

Pharmaceutically acceptable salts include, but are not limited to, acid addition salts, such as those made with hydrochloric, methylsulfonic, hydrobromic, hydroiodic, perchloric, sulfuric, nitric, phosphoric, acetic, propionic, glycolic, lactic, pyruvic, malonic, succinic, fumaric, tartaric, citric, benzoic, carbonic, cinnamic, mandelic, methanesulfonic, ethanesulfonic, hydroxyethanesulfonic, benezenesulfonic, p-toluene sulfonic, cyclohexane-sulfamic, salicyclic, p-aminosalicylic, 2-phenoxybenzoic, and 2-acetoxybenzoic acid. All of these salts (or other similar salts) may be prepared by conventional means. The nature of the salt is not critical, provided that it is non-toxic and does not substantially interfere with the desired pharmacological activity.

The term "analog" or "derivative" is used herein in the conventional pharmaceutical sense, to refer to a molecule that structurally resembles a reference molecule (such as neramexane), but has been modified in a targeted and controlled manner to replace one or more specific substituents of the referent molecule with an alternate substituent, thereby generating a molecule which is structurally similar to the reference molecule. Synthesis and screening of analogs (e.g., using structural and/or biochemical analysis), to identify slightly modified versions of a known compound which may have improved or biased traits (such as higher potency and/or selectivity at a specific targeted receptor type, greater ability to penetrate mammalian blood-brain barriers, fewer side effects, etc.) is a drug design approach that is well known in pharmaceutical chemistry.

The term "treat" is used herein to mean to relieve or alleviate at least one symptom of a disease in a subject. Within the meaning of the present invention, the term "treat" also denotes to arrest, delay the onset (i.e., the period prior to clinical manifestation of a disease) and/or reduce the risk of developing or worsening a disease.

The term "therapeutically effective" applied to dose or amount refers to that quantity of a compound or pharmaceutical composition that is sufficient to result in a desired activity upon administration to a mammal in need thereof.

The phrase "pharmaceutically acceptable", as used in connection with compositions of the invention, refers to molecular entities and other ingredients of such compositions that are physiologically tolerable and do not typically produce untoward reactions when administered to a mammal (e.g., human). Typically, the term "pharmaceutically acceptable" means approved by a regulatory agency of the Federal or a state government or listed in the U.S. Pharmacopeia or other generally recognized pharmacopeia for use in mammals, and more particularly in humans.

The term "carrier" applied to pharmaceutical compositions of the invention refers to a diluent, excipient, or vehicle with which an active compound (e.g., neramexane) is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Suitable pharmaceutical carriers are described in "Remington's Pharmaceutical Sciences" by A. R. Gennaro, $20^{th}$ Edition.

The term "about" or "approximately" usually means within 20%, alternatively within 10%, including within 5% of a given value or range. Alternatively, especially in biological systems, the term "about" means within about a log (i.e., an order of magnitude), including within a factor of two of a given value.

In conjunction with the methods of the present invention, also provided are pharmaceutical compositions comprising a therapeutically effective amount of a 1-amino-alkylcyclohexane derivative (e.g., neramexane). The compositions of the invention may further comprise a carrier or excipient (all pharmaceutically acceptable). The compositions may be formulated for once-a-day administration, twice-a-day administration, or three times a day administration.

The active ingredient (e.g., neramexane, such as neramexane mesylate) or the composition of the present invention may be used for the treatment of at least one of the mentioned disorders, wherein the medicament is adapted to or appropriately prepared for a specific administration as disclosed herein (e.g., to once-a-day, twice-a-day administration, or three times a day administration). For this purpose the package leaflet and/or the patient information contains corresponding information.

The active ingredient (e.g., neramexane, such as neramexane mesylate) or the composition of the present invention may be used for the manufacture of a medicament for the treatment of at least one of the mentioned disorders, wherein the medicament is adapted to or appropriately prepared for a specific administration as disclosed herein (e.g., to once-a-day, twice-a-day administration, or three times a day administration). For this purpose the package leaflet and/or the patient information contains corresponding information.

According to the present invention, the dosage form of the 1-amino-alkylcyclohexane derivative (e.g., neramexane) may be a solid, semisolid, or liquid formulation according to the following.

The 1-amino-alkylcyclohexane derivatives of the present invention (e.g., neramexane) may be administered orally, topically, parenterally, or mucosally (e.g., buccally, by inhalation, or rectally) in dosage unit formulations containing conventional non-toxic pharmaceutically acceptable carriers. In another embodiment for administration to pediatric subjects, the 1-amino-alkylcyclohexane derivative may be formulated as a flavored liquid (e.g., peppermint flavor). The 1-amino-alkylcyclohexane derivatives of the present invention may be administered orally in the form of a capsule, a tablet, or the like, or as a semi-solid, or liquid formulation (see Remington's Pharmaceutical Sciences, 20$^{th}$ Edition, by A. R. Gennaro).

For oral administration in the form of a tablet or capsule, the 1-amino-alkylcyclohexane derivatives of the present invention (e.g., neramexane) may be combined with a non-toxic, pharmaceutically acceptable excipients such as binding agents (e.g., pregelatinized maize starch, polyvinylpyrrolidone or hydroxypropyl methylcellulose); fillers (e.g., lactose, sucrose, glucose, mannitol, sorbitol and other reducing and non-reducing sugars, microcrystalline cellulose, calcium sulfate, or calcium hydrogen phosphate); lubricants (e.g., magnesium stearate, talc, or silica, steric acid, sodium stearyl fumarate, glyceryl behenate, calcium stearate, and the like); disintegrants (e.g., potato starch or sodium starch glycolate); or wetting agents (e.g., sodium lauryl sulphate), coloring and flavoring agents, gelatin, sweeteners, natural and synthetic gums (such as acacia, tragacanth or alginates), buffer salts, carboxymethylcellulose, polyethyleneglycol, waxes, and the like.

The tablets may be coated with a concentrated sugar solution which may contain e.g., gum arabic, gelatine, talcum, titanium dioxide, and the like. Alternatively, the tablets can be coated with a polymer that dissolves in a readily volatile organic solvent or mixture of organic solvents. In specific embodiments, neramexane is formulated in immediate-release (IR) or modified-release (MR) tablets. Immediate release solid dosage forms permit the release of most or all of the active ingredient over a short period of time, such as 60 minutes or less, and make rapid absorption of the drug possible (immediate release formulations of 1-amino-alkylcyclohexanes such as neramexane are disclosed in US Published Application Nos. 2006/0002999 and 2006/0198884, the subject matter of which is hereby incorporated by reference). Modified release solid oral dosage forms permit the sustained release of the active ingredient over an extended period of time in an effort to maintain therapeutically effective plasma levels over similarly extended time intervals and/or to modify other pharmacokinetic properties of the active ingredient (modified release formulations of neramexane are disclosed in US Published Application No. 2007/0141148, the subject matter of which is hereby incorporated by reference). For example, neramexane mesylate may be formulated in a modified release dosage form (including modified release tablets) to provide a 50 mg dose of neramexane mesylate.

For the formulation of soft gelatin capsules, the 1-amino-alkylcyclohexane derivatives of the present invention (e.g., neramexane) may be admixed with e.g., a vegetable oil or poly-ethylene glycol. Hard gelatin capsules may contain granules of the active substances using either the above mentioned excipients for tablets e.g., lactose, saccharose, sorbitol, mannitol, starches (e.g., potato starch, corn starch or amylopectin), cellulose derivatives or gelatine. Also liquids or semisolids of the drug can be filled into hard gelatine capsules.

The 1-amino-alkylcyclohexane derivatives of the present invention (e.g., neramexane) can also be introduced in microspheres or microcapsules, e.g., fabricated from polyglycolic acid/lactic acid (PGLA) (see, e.g., U.S. Pat. Nos. 5,814,344; 5,100,669 and 4,849,222; PCT Publications No. WO 95/11010 and WO 93/07861). Biocompatible polymers may be used in achieving controlled release of a drug, include for example, polylactic acid, polyglycolic acid, copolymers of polylactic and polyglycolic acid, polyepsilon caprolactone, polyhydroxybutyric acid, polyorthoesters, polyacetals, polyhydropyrans, polycyanoacrylates, and cross-linked or amphipathic block copolymers of hydrogels.

Formulation of the 1-amino-alkylcyclohexane derivatives of the present invention in a semi-solid or liquid form may also be used. The 1-amino-alkylcyclohexane derivative (e.g., neramexane) may constitute between 0.1 and 99% by weight of the formulation, more specifically between 0.5 and 20% by weight for formulations intended for injection and between 0.2 and 50% by weight for formulations suitable for oral administration.

In one embodiment of the invention, the 1-amino-alkylcyclohexane derivative (e.g., neramexane) is administered in a modified release formulation. Modified release dosage forms provide a means for improving patient compliance and for ensuring effective and safe therapy by reducing the incidence of adverse drug reactions. Compared to immediate release dosage forms, modified release dosage forms can be used to prolong pharmacologic action after administration, and to reduce variability in the plasma concentration of a drug throughout the dosage interval, thereby eliminating or reducing sharp peaks.

A modified release form dosage may comprise a core either coated with or containing a drug. The core being is then coated with a release modifying polymer within which the drug is dispersed. The release modifying polymer disintegrates gradually, releasing the drug over time. Thus, the outer-most layer of the composition effectively slows down and thereby regulates the diffusion of the drug across the coating layer when the composition is exposed to an aqueous environment, i.e. the gastrointestinal tract. The net rate of diffusion of the drug is mainly dependent on the ability of the gastric fluid to penetrate the coating layer or matrix and on the solubility of the drug itself.

In another embodiment of the invention, the 1-amino-alkylcyclohexane derivative (e.g., neramexane) is formulated in an oral, liquid formulation. Liquid preparations for oral administration can take the form of, for example, solutions, syrups, emulsions or suspensions, or they can be presented as a dry product for reconstitution with water or other suitable vehicle before use. Preparations for oral administration can be suitably formulated to give controlled or postponed release of the active compound. Oral liquid formulations of 1-amino-alkylcyclohexanes, such as neramexane, are described in PCT International Application No. PCT/US2004/037026, the subject matter of which is hereby incorporated by reference.

For oral administration in liquid form, 1-amino-alkylcyclohexane derivatives of the present invention (e.g., neramexane) may be combined with non-toxic, pharmaceutically acceptable inert carriers (e.g., ethanol, glycerol, water), suspending agents (e.g., sorbitol syrup, cellulose derivatives or hydrogenated edible fats), emulsifying agents (e.g., lecithin or acacia), non-aqueous vehicles (e.g., almond oil, oily esters, ethyl alcohol or fractionated vegetable oils), preservatives (e.g., methyl or propyl-p-hydroxybenzoates or sorbic acid), and the like. Stabilizing agents such as antioxidants (BHA, BHT, propyl gallate, sodium ascorbate, citric acid) can also be added to stabilize the dosage forms. For example, solutions may contain from about 0.2% to about 20% by weight of neramexane, with the balance being sugar and mixture of ethanol, water, glycerol and propylene glycol. Optionally, such liquid formulations may contain coloring agents, flavoring agents, saccharine and carboxymethyl-cellulose as a thickening agent or other excipients.

In another embodiment, a therapeutically effective amount of a 1-amino-alkylcyclohexane derivative (e.g., neramexane) is administered in an oral solution containing a preservative, a sweetener, a solubilizer, and a solvent. The oral solution may include one or more buffers, flavorings, or additional excipients. In a further embodiment, a peppermint or other flavoring is added to the neramexane derivative oral liquid formulation.

For administration by inhalation, 1-amino-alkylcyclohexane derivatives (e.g., neramexane) of the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

Solutions for parenteral applications by injection may be prepared in an aqueous solution of a water-soluble pharmaceutically acceptable salt of the active substances, e.g., in a concentration of from about 0.5% to about 10% by weight. These solutions may also contain stabilizing agents and/or buffering agents and may conveniently be provided in various dosage unit ampoules.

The formulations of the invention may be delivered parenterally, i.e., by intravenous (i.v.), intracerebroventricular (i.c.v.), subcutaneous (s.c.), intraperitoneal (i.p.), intramuscular (i.m.), subdermal (s.d.), or intradermal (i.d.) administration, by direct injection, via, for example, bolus injection or continuous infusion. Formulations for injection can be presented in unit dosage form, e.g., in ampoules or in multi-dose containers, with an added preservative. Alternatively, the active ingredient may be in powder form for reconstitution with a suitable vehicle, e.g., sterile pyrogen-free water, before use.

The invention also provides a pharmaceutical pack or kit comprising one or more containers containing a 1-amino-alkylcyclohexane derivative (e.g., neramexane) and, optionally, more of the ingredients of the formulation. In a specific embodiment, neramexane is provided as an oral solution (2 mg/ml) for administration with the use of a 2 teaspoon capacity syringe (dosage KORC®). Each oral syringe has blue hatch marks for measurement, with lines on the right side of the syringe (tip down) representing tsp units, and those on the left representing ml units.

The optimal therapeutically effective amount may be determined experimentally, taking into consideration the exact mode of administration, from in which the drug is administered, the indication toward which the administration is directed, the subject involved (e.g., body weight, health, age, sex, etc.), and the preference and experience of the physician or veterinarian in charge.

Dosage units for rectal application may be solutions or suspensions or may be prepared in the form of suppositories or retention enemas comprising neramexane in a mixture with a neutral fatty base, or gelatin rectal capsules comprising the active substances in admixture with vegetable oil or paraffin oil.

Toxicity and therapeutic efficacy of the compositions of the invention may be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it may be expressed as the ratio $LD_{50}/ED_{50}$. Compositions that exhibit large therapeutic indices are preferred.

Suitable daily doses of the active compounds of the invention in therapeutic treatment of humans are about 0.01-10 mg/kg bodyweight on peroral administration and 0.001-10 mg/kg bodyweight on parenteral administration. For example; for adults, suitable daily doses of neramexane (e.g. neramexane mesylate) are within the range from about 5 mg to about 150 mg per day, such as from about 5 mg to about 120 mg, from about 5 mg to about 100 mg, or from about 5 mg to about 75 mg, or from about 5 mg to about 50 mg, such as 25 mg or 37.5 mg or 50 mg, per day. For example the daily dose may be body weight-adjusted such as 50 mg/day up to 90 kg body weight or 75 mg/day for patients with a body weight of ≥90 kg. An equimolar amount of another pharmaceutically acceptable salt, a solvate, an isomer, a conjugate, a prodrug or a derivative thereof, such as neramexane hydrochloride, is also suitable. For pediatric subjects aged 4-14, neramexane (e.g. neramexane mesylate) may be administered as an oral, liquid dosage form, at about 0.5 mg/day, up to a maximum dose of 10 mg/day.

The daily doses indicated herein may be administered, for example, as one or two dosing units once, twice or three times per day. Suitable doses per dosage unit may therefore be the daily dose divided (for example, equally) between the number of dosage units administered per day, and will thus typically be about equal to the daily dose or one half, one third, one quarter or one sixth thereof. Dosages per dosage unit may thus be calculated from each daily dosage indicated herein. A daily dose of 5 mg, for example may be seen as providing a dose per dosage unit of, for example, about 5 mg, 2.5 mg, 1.67 mg, 1.25 mg and 0.83 mg, depending upon the dosing regimen chosen. Correspondingly, a dosage of 150 mg per day corresponds to dosages per dosing unit of, for example, about 150 mg, 75 mg, 50 mg, 37.5 mg, and 25 mg for corresponding dosing regimens.

Treatment duration may be short-term, e.g., several weeks (for example 8-14 weeks), or long-term until the attending physician deems further administration no longer is necessary.

The 1-amino-alkylcyclohexane derivatives of the present invention (e.g., neramexane) may be administered as a monotherapy, or in combination with another agent prescribed for the treatment of tinnitus.

The term "combination" applied to active ingredients is used herein to define a single pharmaceutical composition (formulation) comprising two active agents (e.g., a pharmaceutical composition comprising a 1-amino-alkylcyclohexane derivative, such as neramexane, and another agent prescribed for the treatment of tinnitus) or two separate pharmaceutical compositions, each comprising an active agent (e.g. a pharmaceutical composition comprising a 1-amino-alkylcyclohexane derivative, such as neramexane, or another agent prescribed for the treatment of tinnitus), to be administered conjointly.

Within the meaning of the present invention, the term "conjoint administration" is used to refer to administration of 1-amino-alkylcyclohexane derivative, such as neramexane, and a second active agent (e.g. another agent prescribed for the treatment of cochlear tinnitus) simultaneously in one composition, or simultaneously in different compositions, or sequentially. For the sequential administration to be considered "conjoint", however, 1-amino-alkylcyclohexane derivative, such as neramexane, and the second active agent must be administered separated by a time interval which still permits the resultant beneficial effect for treating cochlear tinnitus in a mammal.

EXAMPLES OF REPRESENTATIVE FORMULATIONS

With the aid of commonly used solvents, auxiliary agents and carriers, active ingredients may be processed into tablets, coated tablets, capsules, drip solutions, suppositories, injection and infusion preparations, and the like and can be therapeutically applied by the oral, rectal, parenteral, and additional routes. Tablets suitable for oral administration may be prepared by conventional tabletting techniques. The following example is given by way of illustration only and is not to be construed as limiting.

Formulation Example 1

Neramexane Mesylate Immediate Release Tablets

The following tables provide the make-up of neramexane immediate release tablets in 12.5, 25.0, 37.5, and 50.0 mg dosages, including active components, coating agents, and other excipients.

TABLE 1

Neramexane mesylate, 12.5 mg film coated tablets

| Component | Amount [mg] | Function |
| --- | --- | --- |
| Neramexane mesylate | 12.50 | Active pharmaceutical ingredient |
| Cellulose microcrystalline | 103.25 | Binder |
| Croscarmellose sodium | 6.25 | Disintegrant |
| Silicon dioxide, colloidal | 1.25 | Flow promoter |
| Talc | 1.25 | Glident |
| Magnesium stearate | 0.50 | Lubricant |
| core weight | 125.00 | |
| Coating (HPMC), Opadry or Sepifilm | 5.00 | Coating |
| Coat weight | 5.00 | |
| coated tablet total weight | 130.00 | |

TABLE 2

Neramexane mesylate, 25.0 mg film coated tablets

| Component | Amount [mg] | Function |
| --- | --- | --- |
| Neramexane mesylate | 25.00 | Active pharmaceutical ingredient |
| Cellulose microcrystalline | 206.50 | Binder |
| Croscarmellose sodium | 12.5 | Disintegrant |
| Silicon dioxide, colloidal | 2.50 | Flow promoter |
| Talc | 2.50 | Glident |
| Magnesium stearate | 1.00 | Lubricant |
| core weight | 250.00 | |
| Coating (HPMC), Opadry or Sepifilm | 10.00 | Coating |
| Coat weight | 10.00 | |
| coated tablet total weight | 260.00 | |

TABLE 3

Neramexane mesylate, 37.5 mg film coated tablets

| Component | Amount [mg] | Function |
| --- | --- | --- |
| Neramexane mesylate | 37.50 | Active pharmaceutical ingredient |
| Cellulose microcrystalline | 309.75 | Binder |
| Croscarmellose sodium | 18.75 | Disintegrant |
| Silicon dioxide, colloidal | 3.75 | Flow promoter |
| Talc | 3.75 | Glident |
| Magnesium stearate | 1.50 | Lubricant |
| core weight | 375.00 | |
| Coating (HPMC), Opadry or Sepifilm | 15.00 | Coating |
| Coat weight | 15.00 | |
| coated tablet total weight | 390.00 | |

TABLE 4

Neramexane mesylate, 50.0 mg film coated tablets

| Component | Amount [mg] | Function |
| --- | --- | --- |
| Neramexane mesylate | 50.00 | Active pharmaceutical ingredient |
| Cellulose microcrystalline | 413.00 | Binder |
| Croscarmellose sodium | 25.00 | Disintegrant |
| Silicon dioxide, colloidal | 5.00 | Flow promoter |
| Talc | 5.00 | Glident |
| Magnesium stearate | 2.00 | Lubricant |
| core weight | 500.00 | |
| Coating (HPMC), Opadry or Sepifilm | 20.00 | Coating |
| Coat weight | 20.00 | |
| coated tablet total weight | 520.00 | |

The following example illustrates the invention without limiting its scope.

Example 1

Double Blind Placebo Controlled Pilot Trial of Neramexane for Treatment of Tinnitus The objective of this pilot project was to conduct a clinical trial to assess the efficacy of neramexane as a treatment for tinnitus. The primary objective of this study was to compare the efficacy, tolerability and safety of neramexane mesylate at three different dosages (25, 50 or 75 mg/d) with placebo in subjects with subjective tinnitus of at least moderate severity.

Study Design

In a double-blind, multicenter, randomized, placebo-controlled, parallel-group study, the efficacy of neramexane in subjects suffering from tinnitus of at least moderate severity was assessed. Approximately 100 patients, who fulfilled particular inclusion criteria and met none of particular exclusion criteria, were randomized to each of four double-blind treatment groups (neramexane mesylate 25, 50, 75 mg/d or placebo), resulting in approximately 400 patients in total.

The double-blind, 16-week treatment period consisted of a 4-week uptitration period and a 12-week fixed-dose treatment period at unchanged maintenance b.i.d. dosing. In case of poor tolerability, however, the investigator could consider a dose reduction by 25 mg/d (or placebo, respectively). After the treatment phase, there was a 4-week follow-up period with no active treatment and concomitant therapy restrictions. In total, this study involved seven study visits: screening, baseline, and at the end of weeks 4, 8, 12, 16, and 20.

The scheduled visits for evaluation of each patient were as follows:

Visit 1 (screening): After signing the consent form, the subject underwent a physical examination and clinical laboratory testing. Patient eligibility for the study was evaluated via a check of inclusion/exclusion criteria. An initial Tinnitus Interview was conducted. The subject also completed a Tinnitus-Beeinträchtigungs-Fragebogen (THF-12) (i.e., a 12-item German modified and validated version (Greimel K V et al., Tinnitus-Beeinträchtigungs-Fragebogen (THF-12). Manual. Frankfurt am Main: Swets & Zeitlinger B. V.; 2000) of the 25-item Tinnitus Handicap Inventory or THI (Newman C W, et al. Development of the Tinnitus Handicap Inventory. Arch Otolaryngol Head Neck Surg 1996; 122(2): 143-148; Newman C W, et al. Psychometric adequacy of the Tinnitus Handicap Inventory (THI) for evaluating treatment outcome. J Am Acad Audiol 1998; 9(2): 153-160.)), a Hospital Anxiety and Depression Scale—Depression Subscale (HADS-D) Questionnaire and a Hyperacusis (Geräuschüberempfindlichkeit-Fragenbogen (GÜF)) Questionnaire (if applicable).

Visit 2 (baseline): The subject was asked about adverse events and changes in concomitant medication/disease, which events/changes were documented. The subject was evaluated for study eligibility based on a review of the inclusion/exclusion criteria. Trial procedures as well as allowed and forbidden concomitant medications were reviewed with the subject. An initial Tinnitus Interview was conducted. The subject also completed a THF-12, HADS-D Questionnaire and GÜF Questionnaire (if applicable). The subject was enrolled in the study and study medication (placebo or neramexane) was dispensed as described below.

Visit 3 (Week 4): This visit occurred at the end of the 4-week up-titration sequence. The subject was asked about adverse events and changes in concomitant medication/disease, which events/changes were documented. A follow-up Tinnitus Interview was conducted. The subject also completed a THF-12, HADS-D Questionnaire and GÜF Questionnaire (if applicable). Medication compliance was assessed, and medication for the next 4 weeks was dispensed as described below.

Visit 4 (Week 8): This visit occurred at the end of the first 4-week fixed-dose double-blind treatment period. The subject was asked about adverse events and changes in concomitant medication/disease, which changes are documented. Blood samples were collected in order to determine neramexane pre-dose concentration. A follow-up Tinnitus Interview was conducted. The subject also completed a THF-12, HADS-D Questionnaire and GÜF Questionnaire (if applicable). Medication compliance was assessed and, medication for the next 4 weeks was dispensed as described below.

Visit 5 (Week 12): This visit occurred at the end of the second 4-week fixed-dose double-blind treatment period. The subject was asked about adverse events and changes in concomitant medication/disease, which changes are documented. A follow-up Tinnitus Interview was conducted. The subject also completed a THF-12, HADS-D Questionnaire and GÜF Questionnaire (if applicable). Medication compliance was assessed and, medication for the next 4 weeks was dispensed as described below.

Visit 6 (Week 16, end of treatment): This visit occurred at the end of the 12-week fixed-dose double-blind treatment period. The subject was asked about adverse events and changes in concomitant medication/disease, which changes are documented. A clinical laboratory evaluation was performed. A follow-up Tinnitus Interview was conducted, and the subject completed a THF-12, HADS-D Questionnaire and GÜF Questionnaire (if applicable). Pure-tone audiometry (air conduction) was also conducted.

Visit 7 (Week 20): This visit occurred at the end of the 4-week follow-up period after the last study medication dose. Review of concomitant medications as well as the occurrence of adverse events since the last visit is conducted with subject. A follow-up Tinnitus Interview was conducted, and the subject completed a THF-12, HADS-D Questionnaire and GÜF Questionnaire (if applicable).

Administration of Neramexane

Neramexane mesylate immediate release tablets (12.5 mg and 25 mg) and matching placebo tablets were administered as film coated tablets.

Medication was supplied in blister boxes that were dispensed from Visit 2 to Visit 5. Each blister box contained 4 blister cards for 4 treatment weeks and 1 blister card as reserve. Blister cards were identified by treatment weeks. Daily medication within the blister cards were identified per day. Study medication for each study day consisted of 4 separate tablets. One blister card contained of 32 tablets (7×4 tablets, 4 tablets per day, and a reserve of 4 tablets for one day). One package of medication per patient consisted of 5 boxes. Box 2 was added as reserve medication for box 1 (uptitration period) and was only to be dispensed if the subject lost a blister card of box 1 or the whole box.

Study medication was dispensed at Visit 2 (baseline, day 0). Each patient received one blister box containing 5 blister cards (including one reserve blister) of double-blind study medication (i.e., 32 tablets). Subjects were instructed to take 2 tablets twice daily (4 tablets/d), beginning the day after dispensing of the study medication, until they returned for their next study visit (Visit 3). For those subjects assigned to receive active medication, some placebo tablets were incorporated into the dosing regimen to ensure blinding during the uptitration period. The target fixed-maintenance dose of 25, 50, or 75 mg/d was administered starting with the fifth week of double-blind treatment and was continued throughout the study. At each of the subsequent visits (Visits 3, 4, and 5, corresponding to end of week 4, 8 and 12) patients received another blister box containing 5 blister cards for the 4 week intervals, with double-blind medication for the intervening treatment period until the next study visit. The dosing schedule is shown in Table 5.

Throughout the double-blind treatment period, patients were to continue to take 2×2 tablets of medication daily at a constant interval of 12 hours. In case the patient had already taken the morning dose of study medication on the day of Visits 4 and 6 (Week 8 and Week 16), no scheduled blood sampling was to be done. The investigator had to redispense a sufficient amount of study medication. The patient should continue to take 2 by 2 tablets at a constant interval of 12 hours and had return for pre-dose Neramexane blood sampling within the time window of Visits 4 and 6.

TABLE 5

Administration of Neramexane mesylate

| Treatment group | 4-week double-blind up-titration period | | | | 12-week fixed-dose double-blind period | 4-week follow-up |
| --- | --- | --- | --- | --- | --- | --- |
| | Week 1 | Week 2 | Week 3 | Week 4 | Weeks 5-16 | Weeks 17-20 |
| High-dose | 12.5/0 | 12.5/12.5 | 25/12.5 | 25/25 | 37.5/37.5 (75 mg/d) | — |
| Medium-dose | 12.5/0 | 12.5/12.5 | 12.5/12.5 | 25/12.5 | 25/25 (50 mg/d) | — |
| Low-dose | 12.5/0 | 12.5/0 | 12.5/0 | 12.5/0 | 12.5/12.5 (25 mg/d) | — |
| Placebo | 0/0 | 0/0 | 0/0 | 0/0 | 0/0 | — |

(xx/xx) refers to the morning/evening dose in mg, respectively

In case of poor tolerability the investigator could consider a dose reduction of 25 mg/d by omitting the bigger tablet in the morning which constituted an effective dose reduction only in the 75 mg/d and 50 mg/d neramexane mesylate groups. After omitting the bigger tablet (25 mg or placebo, respectively) of the morning dose, these patients could then continue the course of the study as scheduled, while receiving only one smaller tablet as the morning dose (12.5 mg or placebo, respectively) and 2 tablets of different sizes (12.5 mg, 25 mg or placebo, respectively) as the evening dose. The dose was to be kept stable until the end of the study.

Subjects were instructed to take study medication always at an individually convenient, but stable time point throughout the study course and at a constant dosing interval of 12 hours whenever possible (e.g. 6:00 h and 18:00 h or 8:00 h and 20:00 h). At each study visit, the investigator enquired the time points of study medication intake on the preceding day. At the end of week 4, 8, 12, and 16 (or upon early termination), patients returned to the study site bringing their blister boxes containing 5 blister cards with them for an assessment of medication compliance.

Efficacy

Primary Outcome

The change in THF-12 total score from baseline (Visit 2) to the endpoint visit (Visit 6, i.e. Week 16) was the primary efficacy endpoint in this study.

Secondary Outcomes

THF-12 total score (values and absolute change from baseline) at all post-baseline visits except the endpoint visit.

Change in the THF-12 total score from Week 16 to Week 20 (values and absolute changes).

THF-12 factorial scores (values and absolute change from baseline, including the change from Week 16 to Week 20) at all post-baseline visits.

Hyperacusis questionnaire GÜF ("Geräuschüberempfindlichkeits-Fragebogen"), values and absolute change from baseline, including the change from Week 16 to Week 20, total and factorial scores at all post-baseline visits if hyperacusis was present.

Clinical global impression of change: item 27 of the tinnitus follow-up interview was summarized after dichotomization of the responses in any improvement (values 1, 2, 3) versus no improvement (values 4, 5, 6, 7) and in marked improvement (values 1, 2) versus no marked improvement (values 3, 4, 5, 6, 7).

Total score of HADS-D as well as the depression and anxiety subscale scores (values and absolute change from baseline, also the change from week 16 to week 20) at all post-baseline visits.

Values of tinnitus interview (initial and follow-up) at all post-baseline visits; absolute change from baseline and change from Week 16 to Week 20 for items 8, 9, 10, 19, 20, 21, 24, 25 and 26 of the follow-up interview.

Data Analysis

All efficacy analyses were performed on the ITT population using the last-observation-carried-forward (LOCF) approach. For sensitivity purposes an analysis of the per-protocol set and of observed cases was performed additionally. All statistical tests used for testing the primary efficacy (confirmatory testing) and secondary efficacy criteria (exploratory), and all other statistical tests used for exploratory analyses were two-sided hypothesis tests performed at the 5% significance level. For all variables standard descriptive statistics were calculated.

Change from baseline (Visit 2) to Week 16 in THF-12 total score was analyzed using a two-way ANCOVA model with treatment group and study centers as factors and baseline THF-12 total score as covariate.

For secondary efficacy parameters, the comparison between neramexane and placebo was performed, if appropriate, by visit using a two-way ANCOVA with treatment group and study center as factors and the corresponding baseline value of the efficacy parameter as covariate.

This clinical study showed promising results in terms of efficacy and safety. Moreover, subgroup analyses indicated that subjects who were classified by the respective investigators as suffering from cochlear tinnitus (i.e. tinnitus in the frequency region of the patient's sensorineural hearing loss and a tinnitus sensation level between 3 and 12 dB) responded well to treatment with neramexane. FIG. 1 shows the change in THF-12 score at the end of treatment for the 50 mg dose group compared to placebo. In the same trial, patients who were treated within three (3) to eight (8) months of onset of tinnitus (Table 6) and patients with mild hearing loss (Table 7) showed a better response (effect in treating tinnitus) to neramexane as compared to the total study population (Table 8). Especially in the 50 mg dose group, the improvement (as compared to placebo treatment) in patients whose onset of tinnitus was three to eight months before treatment or who showed a mild hearing loss was markedly higher (−1.9 points difference in each group) and reached statistical significance in the post-hoc analyses (p=0.019 and 0.024), whereas the difference to placebo in the total study population was only 0.8 point and failed to reach statistical significance (p=0.098).

In patients presenting at baseline with clinical symptoms of anxiety or depression, as indicated by a total score of 10 or more measured on the Hospital anxiety and depression scale (HADS), treatment with a 50 or 75 mg daily dose of neramexane monotherapy produced a weaker benefit compared to such treatment in patients with a score below 10 at baseline (Table 9). Since anxiety and depression are common medical problems in tinnitus patients (Reynolds et al., Clin. Otolaryngol., 2004, 29, 628-634), a combination of anti-depressants and anti-anxiety drugs with neramexane may offer additional benefits for the treatment of this subgroup of tinnitus patients.

TABLE 6

Subjects with tinnitus duration 3 to <8 months
Change in the TBF-12 total score (range 0-24) from baseline to week 16 (ITT-LOCF)

| | | Baseline | Week 16 | | | Week 16 Neramexane-Placebo | | |
|---|---|---|---|---|---|---|---|---|
| | | | Actual | Change | | | | |
| ITT-LOCF | n | Mean ± SD | Mean ± SD | Mean ± SD | Change LSMean | LSMean Diff. ± SE | 95% CI | p-value[1] |
| Placebo | 50 | 14.1 ± 3.4 | 11.8 ± 4.6 | −2.3 ± 3.3 | −2.2 | n.a. | n.a. | n.a. |
| 25 mg/d Neramexane | 45 | 14.9 ± 3.8 | 12.3 ± 4.9 | −2.5 ± 3.0 | −2.2 | 0.0 ± 0.8 | [−1.6, 1.5] | 0.983 |
| 50 mg/d Neramexane | 45 | 14.2 ± 3.4 | 10.0 ± 5.1 | −4.2 ± 3.9 | −4.0 | −1.9 ± 0.8 | [−3.4, −0.3] | 0.019 |
| 75 mg/d Neramexane | 41 | 14.0 ± 3.3 | 10.6 ± 5.0 | −3.4 ± 4.0 | −3.3 | −1.1 ± 0.8 | [−2.7, 0.5] | 0.173 |

[1]p-values are derived from an ANCOVA model including baseline as covariate and treatment as well as pooled center as factors.
CI = confidence interval,
Diff. = difference,
ITT = intent-to-treat,
LOCF = last observation carried forward,
LSMean = least square mean (mean adjusted for covariates),
n = number of patients with data,
n.a. = not applicable,
SD = standard deviation,
SE = standard error

TABLE 7

Subjects with mild hearing loss
Change in the TBF-12 total score (range 0-24) from baseline to week 16 (ITT-LOCF)

| | | Baseline | Week 16 | | | Week 16 Neramexane-Placebo | | |
|---|---|---|---|---|---|---|---|---|
| | | | Actual | Change | | | | |
| ITT-LOCF | n | Mean ± SD | Mean ± SD | Mean ± SD | Change LSMean | LSMean Diff. ± SE | 95% CI | p-value[1] |
| Placebo | 42 | 14.8 ± 3.9 | 12.8 ± 5.2 | −2.0 ± 4.3 | −2.0 | n.a. | n.a. | n.a. |
| 25 mg/d Neramexane | 33 | 14.6 ± 4.2 | 13.1 ± 5.8 | −1.5 ± 3.4 | −1.3 | 0.7 ± 0.9 | [−1.2, 2.5] | 0.474 |
| 50 mg/d Neramexane | 43 | 15.3 ± 3.5 | 11.5 ± 5.2 | −3.8 ± 3.9 | −3.9 | −1.9 ± 0.8 | [−3.6, −0.3] | 0.024 |
| 75 mg/d Neramexane | 30 | 13.9 ± 3.1 | 12.0 ± 4.6 | −1.9 ± 3.2 | −1.8 | −0.2 ± 0.9 | [−1.6, 2.1] | 0.797 |

[1]p-values are derived from an ANCOVA model including baseline as covariate and treatment as well as pooled center as factors.
CI = confidence interval,
Diff. = difference,
ITT = intent-to-treat,
LOCF = last observation carried forward,
LSMean = least square mean (mean adjusted for covariates),
n = number of patients with data,
n.a. = not applicable,
SD = standard deviation,
SE = standard error

TABLE 8

Total study population
Change in the TBF-12 total score from baseline to week 16 (ITT-LOCF)

| | | Baseline | Week 16 | | | Week 16 Neramexane-Placebo | | |
|---|---|---|---|---|---|---|---|---|
| | | | Actual | Change | | | | |
| ITT-LOCF | n | Mean ± SD | Mean ± SD | Mean ± SD | Change LSMean | LSMean Diff. ± SE | 95% CI | p-value[1] |
| Placebo | 111 | 14.4 ± 3.7 | 12.0 ± 4.9 | −2.4 ± 3.6 | −2.3 | n.a. | n.a. | n.a. |
| 25 mg/d Neramexane | 106 | 14.4 ± 3.9 | 12.4 ± 5.3 | −2.0 ± 3.4 | −1.8 | 0.5 ± 0.5 | [−0.5, 1.5] | 0.359 |

TABLE 8-continued

Total study population
Change in the TBF-12 total score from baseline to week 16 (ITT-LOCF)

| ITT-LOCF | Baseline | | Week 16 | | | Week 16 Neramexane-Placebo | | |
|---|---|---|---|---|---|---|---|---|
| | n | Mean ± SD | Actual Mean ± SD | Change Mean ± SD | Change LSMean | LSMean Diff. ± SE | 95% CI | p-value[1] |
| 50 mg/d Neramexane | 106 | 14.5 ± 3.3 | 11.2 ± 5.1 | −3.2 ± 4.1 | −3.1 | −0.8 ± 0.5 | [−1.8, 0.2] | 0.098 |
| 75 mg/d Neramexane | 99 | 13.9 ± 3.7 | 11.0 ± 5.1 | −2.9 ± 3.9 | −2.8 | −0.5 ± 0.5 | [−1.6, 0.5] | 0.289 |

[1]p-values are derived from an ANCOVA model including baseline as covariate and treatment as well as pooled center as factors.
CI = confidence interval,
Diff. = difference,
ITT = intent-to-treat,
LOCF = last observation carried forward,
LSMean = least square mean (mean adjusted for covariates),
n = number of patients with data,
n.a. = not applicable,
SD = standard deviation,
SE = standard error

TABLE 9

Change in TBF-12 total score from baseline to week 16-stratified by grouped HADS-D subscales at baseline (ITT-LOCF)

| | 25 mg/d Neramexane (N = 106) | | | 50 mg/d Neramexane (N = 106) | | | 75 mg/d Neramexane (N = 99) | | |
|---|---|---|---|---|---|---|---|---|---|
| | | | | Week 16 Neramexane-Placebo | | | | | |
| | n | LSMean | p-value | n | LSMean | p-value | n | LSMean | p-value |
| Depression subscale | | | | | | | | | |
| 0-7 | 69 | −0.3 | 0.634 | 76 | −1.3 | 0.039 | 69 | −0.9 | 0.153 |
| 8-10 | 22 | 0.6 | 0.600 | 18 | −1.1 | 0.353 | 18 | 0.0 | 0.984 |
| >10 | 15 | 3.9 | 0.043* | 12 | 3.3 | 0.155 | 12 | 0.4 | 0.847 |
| Anxiety subscale | | | | | | | | | |
| 0-7 | 47 | 0.2 | 0.835 | 55 | −0.5 | 0.472 | 51 | 0.1 | 0.892 |
| 8-10 | 30 | −2.3 | 0.022 | 24 | −2.9 | 0.008 | 30 | −3.1 | 0.003 |
| >10 | 29 | 2.3 | 0.020* | 27 | 0.6 | 0.573 | 18 | 0.3 | 0.802 |

*= in favor of placebo
ITT = intent-to-treat,
LOCF = last observation carried forward,
LSMean = least square mean (mean adjusted for covariates),
N = number of patients in respective treatment group,
n = number of patients with data These findings demonstrate that neramexane is effective in treating subjects with tinnitus originating in the cochlea and before the stage of centralisation, and that, therefore, neramexane may be useful in treating patients with cochlear tinnitus.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference.

The invention claimed is:

1. A method of treating tinnitus in a subject in need thereof, comprising oral administration of an effective amount of a 1-amino-alkylcyclohexane derivative selected from neramexane and pharmaceutically acceptable salts thereof, wherein treatment occurs within three to twelve months of onset of tinnitus.

2. The method of claim 1, wherein treatment occurs within three to eight months of onset of tinnitus.

3. The method of claim 1, wherein the tinnitus is associated with hearing loss.

4. The method of claim 1, wherein the tinnitus is associated with mild hearing loss.

5. The method of claim 1, wherein the tinnitus is cochlear tinnitus.

6. The method of claim 1, wherein the 1-amino-alkylcyclohexane derivative is neramexane mesylate.

7. The method of claim 6, wherein neramexane mesylate is administered in a range from about 5 mg to about 150 mg/day.

8. The method of claim 6, wherein neramexane mesylate is administered in a range from about 5 mg to about 100 mg/day.

9. The method of claim 6, wherein neramexane mesylate is administered in a range from about 5 mg to about mg/day.

10. The method of claim 6, wherein neramexane mesylate is administered at about 50 mg/day.

11. The method of claim 6, wherein neramexane mesylate is administered at about 75 mg/day.

12. The method of claim 1, wherein neramexane or a pharmaceutically acceptable salt thereof is administered once a day, twice a day (b.i.d.), or three times a day.

13. The method of claim 12, wherein neramexane or a pharmaceutically acceptable salt thereof is administered twice a day.

14. The method of claim 1, wherein neramexane or a pharmaceutically acceptable salt thereof is administered in an immediate release formulation.

15. The method of claim 1, wherein neramexane or a pharmaceutically acceptable salt thereof is administered in a modified release formulation.

16. The method of claim 1, further comprising administering an additional pharmaceutical agent which has been shown to be effective in treating or preventing tinnitus and, optionally, at least one pharmaceutically acceptable carrier or excipient.

17. The method of claim 16, wherein the additional pharmaceutical agent is selected from the group consisting of antidepressants, anti-anxiety drugs, dopamine antagonists, Alpha2Delta ligands, and NK1 antagonists.

18. The method of claim 17, wherein the additional pharmaceutical agent is selected from the group consisting of a selective serotonin reuptake inhibitor (SSRI), a serotonin-norepinephrine reuptake inhibitor (SNRI), a noradrenergic and specific serotonergic antidepressant (NASSA), a norepinephrine (noradrenaline) reuptake inhibitor (NRI), a norepinephrine-dopamine reuptake inhibitor; and a serotonin 1A agonist.

19. The method of claim 16, wherein neramexane, or a pharmaceutically acceptable salt thereof, and the additional pharmaceutical agent are administered conjointly.

20. The method of claim 19, wherein neramexane, or a pharmaceutically acceptable salt thereof and the additional pharmaceutical agent are administered in a single formulation.

* * * * *